US006932830B2

(12) United States Patent
Ungs

(10) Patent No.: US 6,932,830 B2
(45) Date of Patent: Aug. 23, 2005

(54) DISC SHAPED FILTER

(75) Inventor: Mark T. Ungs, Minnetonka, MN (US)

(73) Assignee: SciMed Life Systems, Inc., Maple Grove, MN (US)

(*) Notice: Subject to any disclaimer, the term of this patent is extended or adjusted under 35 U.S.C. 154(b) by 130 days.

(21) Appl. No.: 10/044,354

(22) Filed: Jan. 10, 2002

(65) Prior Publication Data

US 2003/0130681 A1 Jul. 10, 2003

(51) Int. Cl.$^7$ .......................................... A61M 29/00
(52) U.S. Cl. ........................................... 606/200
(58) Field of Search ................... 606/200, 113, 606/114, 127, 159, 213–215; 128/898

(56) References Cited

U.S. PATENT DOCUMENTS

| 3,472,230 A | 10/1969 | Fogarty |
| 3,952,747 A | 4/1976 | Kimmell, Jr. |
| 3,996,938 A | 12/1976 | Clark, III |
| 4,046,150 A | 9/1977 | Schwartz et al. |
| 4,425,908 A | 1/1984 | Simon |
| 4,590,938 A | 5/1986 | Segura et al. |
| 4,619,246 A | 10/1986 | Molgaard-Nielsen et al. |
| 4,650,466 A | 3/1987 | Luther |
| 4,706,671 A | 11/1987 | Weinrib |
| 4,723,549 A | 2/1988 | Wholey et al. |
| 4,790,812 A | 12/1988 | Hawkins, Jr. et al. |
| 4,790,813 A | 12/1988 | Kensey |
| 4,794,928 A | 1/1989 | Kletschka |
| 4,807,626 A | 2/1989 | McGirr |
| 4,842,579 A | 6/1989 | Shiber |
| 4,873,978 A | 10/1989 | Ginsburg |
| 4,921,478 A | 5/1990 | Solano et al. |
| 4,921,484 A | 5/1990 | Hillstead |
| 4,926,858 A | 5/1990 | Gifford, III et al. |
| 4,969,891 A | 11/1990 | Gewertz |

(Continued)

FOREIGN PATENT DOCUMENTS

| DE | 28 21 048 | 7/1980 |
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |

(Continued)

OTHER PUBLICATIONS

"Atherosclerotic Disease of the Aortic Arch as a Risk Factor of Recurrent Ischemic Stroke," The New England Journal of Medicine, pp. 1216–1221 (May 1996).

"Endovascular Grafts, Stents Drive Interventional Radiology Growth," *Cardiovascular Device Update*, 2(3):1–12 (Mar. 1996).

"Protruding Atheromas in the Thoracic Aortic and Systemic Embolization," pp. 423–427 American College of Physicians (1991).

(Continued)

*Primary Examiner*—Kevin T. Truong
(74) *Attorney, Agent, or Firm*—Crompton, Seager & Tufte LLC

(57) ABSTRACT

Distal protection filter and method of using the same. A distal protection filter may be coupled to an elongate shaft. The filter includes a filter material coupled to a filter frame. The shape of the filter may be generally cylindrical or disc shaped. The filter material may capture embolic debris generated during an intravascular intervention.

4 Claims, 2 Drawing Sheets

U.S. PATENT DOCUMENTS

| | | |
|---|---|---|
| 4,998,539 A | 3/1991 | Delsanti |
| 5,002,560 A | 3/1991 | Machold et al. |
| 5,011,488 A | 4/1991 | Ginsburg |
| 5,053,008 A | 10/1991 | Bajaj |
| 5,071,407 A | 12/1991 | Termin et al. |
| 5,100,423 A | 3/1992 | Fearnot |
| 5,102,415 A | 4/1992 | Guenther et al. |
| 5,133,733 A | 7/1992 | Rasmussen et al. |
| 5,152,771 A | 10/1992 | Sabbaghian et al. |
| 5,152,777 A | 10/1992 | Goldberg et al. |
| 5,160,342 A | 11/1992 | Reger et al. |
| 5,224,953 A | 7/1993 | Morgentaler |
| 5,329,942 A | 7/1994 | Gunther et al. |
| 5,330,484 A | 7/1994 | Gunther |
| 5,354,310 A | 10/1994 | Garnie et al. |
| 5,376,100 A | 12/1994 | Lefebvre |
| 5,421,832 A | 6/1995 | Lefebvre |
| 5,423,742 A | 6/1995 | Theron |
| 5,449,372 A | 9/1995 | Schmaltz et al. |
| 5,454,833 A | 10/1995 | Boussignac et al. |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,658,296 A | 8/1997 | Bates et al. |
| 5,662,671 A | 9/1997 | Barbut et al. |
| 5,695,519 A | 12/1997 | Summers et al. |
| 5,720,764 A | 2/1998 | Naderlinger |
| 5,728,066 A | 3/1998 | Daneshvar |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,795,322 A | 8/1998 | Bouewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,861,003 A | 1/1999 | Latson et al. |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,951,589 A | 9/1999 | Epstein et al. |
| 5,954,745 A | 9/1999 | Gertler et al. |
| 5,957,952 A | 9/1999 | Gershony et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 * | 1/2001 | Tsugita ................ 606/200 |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 * | 9/2001 | Jang ................ 606/200 |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,344,049 B1 | 2/2002 | Levinson et al. |
| 6,425,909 B1 * | 7/2002 | Dieck et al. ................ 606/200 |
| 6,485,501 B1 * | 11/2002 | Green ................ 606/200 |
| 6,582,448 B1 * | 6/2003 | Boyle et al. ................ 606/200 |
| 2001/0044634 A1 | 11/2001 | Michael et al. |

FOREIGN PATENT DOCUMENTS

| | | |
|---|---|---|
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |

| | | |
|---|---|---|
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | 0 934 729 | 8/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01//67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

"Recognition and Embolic Potential of Intraaortic Atherosclerotic Debris," American College of Cardiology (Jan. 1991).

Cragg, Andrew et al., "A New Percutaneous Vena Cava Filger," *AJR*, 141:601–604 (Sep. 1983).

Cragg, Andrew et al., "Nonsurgical Placement of Arterial Endoprosthesis: A New Technique Using Nitinol Wire," AJR, pp. 261–263 (Apr. 1983).

Diethrich et al., "Percutaneous Techniques for Endoluminal Carotid Interventions," *J. Endovasc. Surg.*, 3:182–202 (1996).

Fadali, A. Moneim, "A filtering device for the prevention of particulate embolization during the course of cardiac surgery," Surgery, 64(3):634–639 (Sep. 1968).

Haissaguerre et al., "Spontaneous Initiation of Atrial Fibrillation by Ectopic Beats Originating in the Pulmonary Veins," *The New England Journal of Medicine*, 339(10):659–666 (Sep. 1988).

Jordan, Jr. et al., "Microemboli Detected by Transcranial Doppler Monitoring . . . ," Cardiovascular Surgery, 7(1)33–38 (Jan. 1999).

Lesh, "Can Catheter Ablation Cure Atrial Fibrillation?" *ACC Current Journal Review*, pp. 38–40 (Sep./Oct. 1997).

Lund et al., "Long–Term Patentcy of Ductus Arteriosus After Balloon Dilation: an Experimental Study," Laboratory Investigation, 69(4):772–774 (Apr. 1984).

Marache et al., "Percutaneous Transluminal Venous Angioplasty . . . ," *American Heart Journal*, 125(2 Pt 1):362–366 (Feb. 1993).

Mazur et al., "Directional Atherectomy with the Omnicath™: A Unique New Catheter System," *Catheterization and Cardiovascular Diagnosis*, 31:17–84 (1994).

Moussa, MD, Issaam "Stents Don't Require Systemic Anticoagulation . . . But the Technique (and Results) Must be Optimal," *Journal of Invasive Cardiol.*, 8(E):3E–7E, (1996).

Nakanishi et al., "Catheter Intervention to Venous System Using Expandable Metallic Stents," *Rinsho Kyobu Geka*, 14(2):English Abstract Only (Apr. 1994).

Onal et al., "Primary Stenting for Complex Atherosclerotic Plaques in Aortic and Iliac Stenoses," *Cardiovascular & Interventional Radiology*, 21(5):386–392 (1998).

Theron et al., "New Type Coaxial Catheter System for Carotid Angioplasty with Cerebral Protection," *American Journal of Neuroradiology*, 11:869–874 (1990).

Tunick et al., "Protruding atherosclerotic plaque in the aortic archo f patients with systemic embolization: A new finding seen by transsesophageal echocardiography," *American Heart Journal* 120(3):658–660 (Sep. 1990).

Waksman et al., "Distal Embolization is Common After Directional Atherectomy . . . ," American Heart Journal, 129(3):430–435 (1995).

Wholey, Mark H. et al., PTA and Stents in the Treatment of Extracranial Circulation, *The Journal of Invasive Cardiology*, 8(E):25E–30E (1996).

* cited by examiner

DISC SHAPED FILTER

BACKGROUND OF THE INVENTION

1. Field of the Invention

The present invention pertains to filtering devices. More particularly, the present invention pertains to devices and methods for filtering embolic debris from a blood vessel.

2. Description of the Related Art

Occluded, stenotic, or narrowed blood vessels may be treated with a number of relatively non-invasive medical procedures. For example, occlusions of blood vessels near the heart may be treated by percutaneous transluminal angioplasty (PTA), percutaneous transluminal coronary angioplasty (PTCA), atherectomy, etc. Similarly, a number of occlusions may occur in other blood vessels located a distance away from the heart. For example, an occlusion may occur within the renal artery between the abdominal aorta and the kidney. Because this vascular region is relatively short in length, an appropriate intervention may necessitate design modifications of current intravascular devices.

When treating occluded or stenotic blood vessels, embolic debris can be separated from the wall of the blood vessel. This debris could block other vascular regions including the renal, neural, and pulmonary vasculature or cause damage to tissue and/or body organs. In order to filter this debris, a number of devices, termed distal protection devices, have been developed.

BRIEF SUMMARY OF THE INVENTION

The present invention pertains to distal protection filter devices. A distal protection filter may be coupled to an elongate shaft. The filter may be generally cylindrical or disc shaped and has a diameter and a length. The length is relatively small and may be smaller than the diameter. The filter may be used to capture embolic debris generated by an intravascular intervention. Aspiration means may be included to aspirate the embolic debris from the filter.

The filter may shift between a generally collapsed configuration and a generally expanded configuration by a number of methods. For example, an outer sheath may be disposed over the shaft and filter such that movement of the sheath relative to the shaft shifts the configuration of the filter. Alternatively, an expansion member may be actuated to shift the filter.

DETAILED DESCRIPTION OF THE INVENTION

Figure 1:
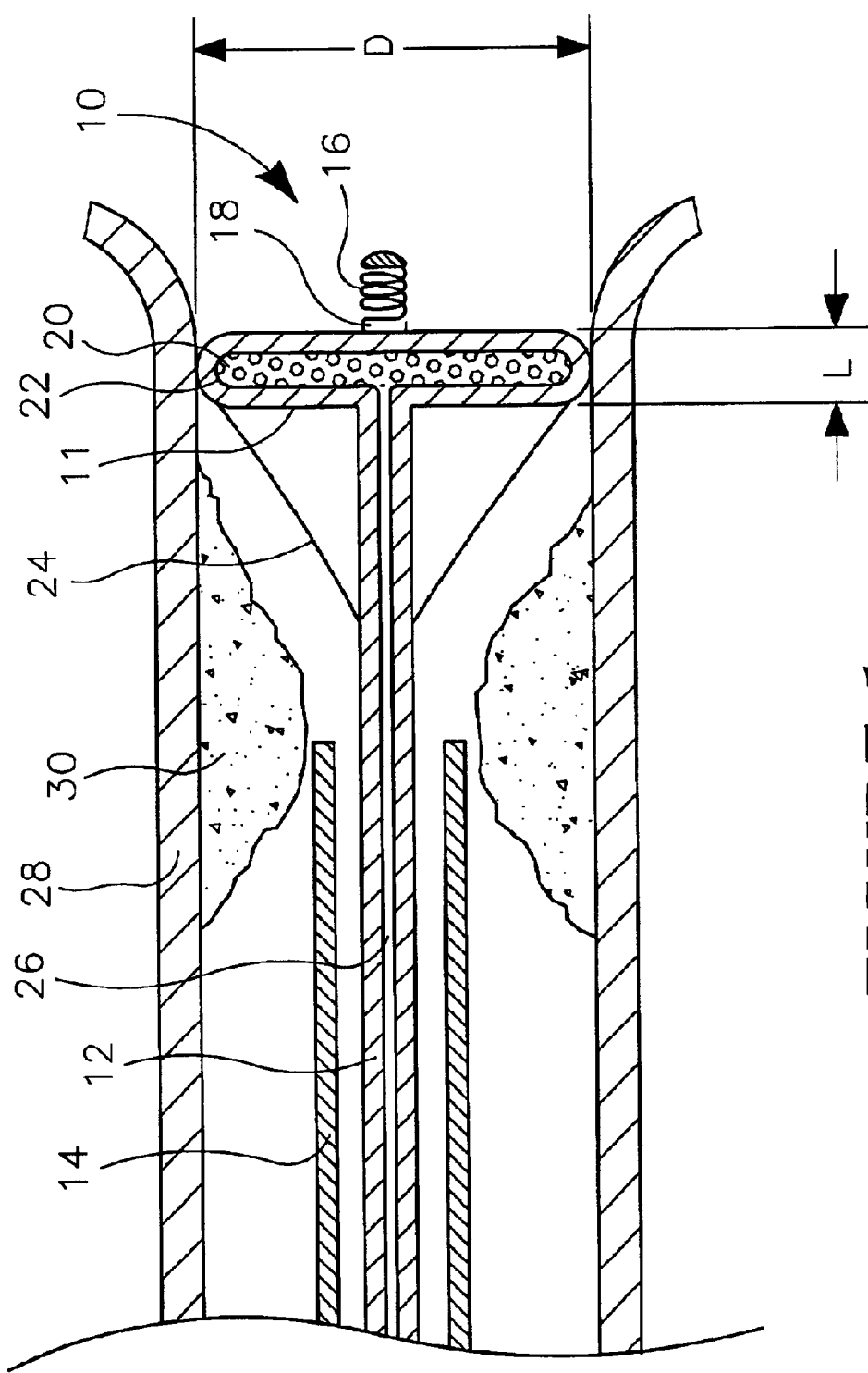
FIG. 1 is a cross sectional view of a distal protection filter.

The following description should be read with reference to the drawings wherein like reference numerals indicate like elements throughout the several views. The detailed description and drawings illustrate example embodiments of the claimed invention.

A number of diagnostic and therapeutic interventions may result in the release of intravascular embolic debris. Several filtering devices have been developed to capture and/or remove this debris. However, some procedures and intravascular locations are not readily accessible to traditional filters. FIG. 1 is a cross sectional plan overview of a disc-shaped distal protection filter device 10. Filter device 10 includes a filter 11 attached to an elongate shaft 12. The design of filter device 10 permits filtering at intravascular locations that might otherwise not be readily accessible by traditional filters.

Shaft 12 may comprise a guidewire or intravascular catheter, similar to any number of those known in the art or as detailed below. A distal spring tip 16 may be disposed at a distal end 18 of shaft 12. Sheath 14 may be generally polymeric and is adapted and configured to be advanced through the vasculature to an area of interest. Once positioned, sheath 14 may be withdrawn proximally to deliver filter 11.

Filter 11 includes a filter material 20 coupled to a filter frame 22. Filter material 20 may be comprised of a polyurethane sheet and include at least one opening that may be, for example, formed by known laser techniques. The holes or openings are sized to allow blood flow therethrough but restrict flow of debris or emboli floating in the body lumen or cavity.

Filter 11 operates between a closed collapsed profile and an open radially-expanded deployed profile for collecting debris in a body lumen. Frame 22 may be self-expanding or otherwise biased to be oriented in the expanded configuration so that withdrawing sheath 14 allows filter 11 to shift to the expanded configuration. A number of methods may be used to shift filter 11 from the expanded configuration to the collapsed configuration. For example, filter 11 may include a plurality of longitudinally-extending struts 24 that extend between frame 20 to shaft 12. It can be appreciated that a number of methods for shifting filter 11 between the collapsed and expanded configuration can be used without departing from the spirit of the invention.

Filter 11 is designed to be disc shaped and/or cylindrical. The cylindrical shape of filter 11 can be understood to have a diameter D and a length L. Diameter D may generally be larger than length L such that filter 11 has a shape that differs from typical conically shaped filters. This characteristic of having a relatively short or thin length may be described as having a "short landing zone" to those in the art. Having a short landing zone can advantageously permit filter 11 to be used at intravascular locations that are relatively short and would otherwise be inaccessible to traditional filters. For example, the length of a portion of the renal artery between the abdominal aorta and the kidney is relatively short. Diagnosis or other interventions at the junction of the renal artery and the kidney would not easily be accomplished by using conically shaped filter because the filter may extend into the kidney, possibly causing damage to the kidney. Because of the shape of filter 11, this location is accessible for filtering by filter 11. A number of additional intravascular locations may similarly benefit from the shape of filter 11.

The dimensions of filter 11 may include diameter D being about 0.10 to 0.30 inches or less and length L may be about 0.01 to 0.15 inches or less. These dimensions are meant to be approximations and provided for illustration purposes. The dimensions may be altered for any one of multiple embodiments.

Shaft 12 may be generally tubular so as to define an aspiration lumen 26 extending therethrough. Aspiration may be important because the thin length of filter 11 may cause filter material 20 to become filled to its capacity with embolic material. Aspiration lumen 26 is connected proximally to a vacuum source and is used to aspirate embolic debris collected on filter material 20.

In use, filter 11 may be contained within sheath 14 and advanced within a blood vessel 28 to an area proximate a lesion 30. Blood vessel 28 may, for example, be the renal artery between the abdominal aorta and the kidney. Once positioned, sheath 14 may be withdrawn from filter 11, permitting filter 11 to shift to the expanded configuration. A therapeutic or diagnostic catheter may be advanced to lesion 30 (i.e., over shaft 12 or sheath 14). Embolic debris released by the intervention is captured by filter material 20. Aspiration lumen 26 may be used to aspirate the debris from filter material 20.

Figure 2:
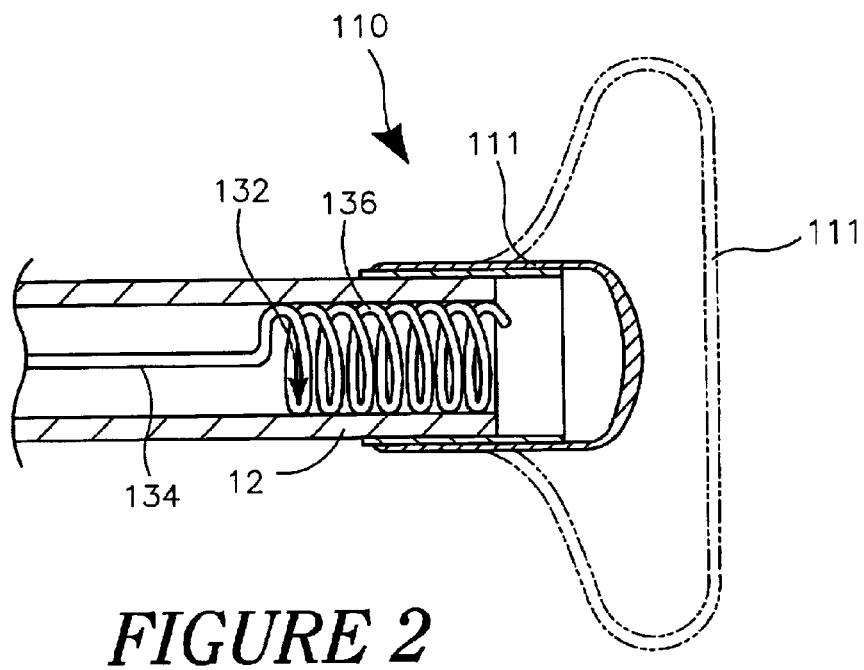
FIG. 2 is a partial cross sectional view of depicting an alternate means for shifting the filter between the expanded and the collapsed configuration.

FIG. 2 is a partial cross section of an alternate filter device 110 that is the same in form and function as device 10 except that filter device 110 includes alternative means for shifting filter 111 between the expanded and the collapsed configuration. Filter 111 may be expanded by actuating a coiled expansion member 132.

Expansion member 132 may include a generally straight proximal portion 134 extending to the proximal end of shaft 12, and a coiled distal portion 136. Distal portion 136 is coupled to filter 111 such that force applied to proximal portion 136 in the distal direction exerts force onto filter 111 in the distal direction and shifts filter 111 distally. Distally shifting filter 111 results in filter 111 shifting to the expanded configuration.

Proximal portion 134 may be connected to a manifold, actuating handle, etc. that permits expansion member 132 to be moved relative to shaft 12 by a clinician. According to this embodiment, expansion member 132 is slidably disposed within shaft 12 and may be moved in either a proximal or distal direction. This may permit the use of filter 111 without the need for a separate delivery or retrieval catheter, which may simplify use and/or overall profile of the device. Moreover, bi-directional motion of expansion member 132 may alloy filter 111 to be positioned in one location, expanded by distal motion of expansion member 132, filter embolic debris, collapsed by proximal motion of expansion member 132, and moved to another location for use.

Figure 3:
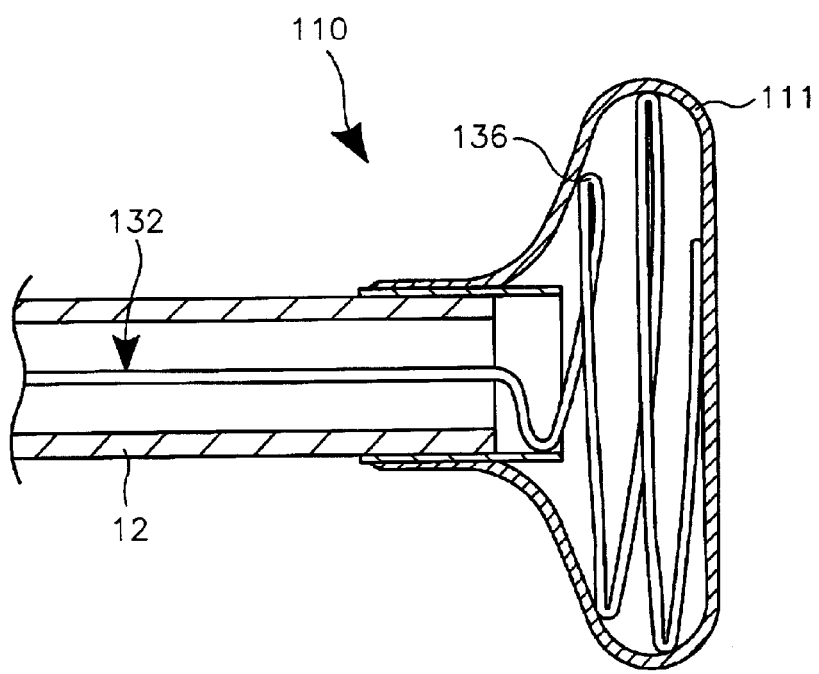
FIG. 3 is a partial cross sectional view of the filter in FIG. 2 in the expanded configuration.

To expand filter 111, distal portion 136 is generally tightly coiled within shaft 12 such that when it is allowed to advance distally out of shaft 12, distal portion 136 expands to expand filter 111 as shown in FIG. 3. It may be beneficial to construct expansion member 132 (or at least distal portion 136) of a shape-memory or superelastic alloy such as nickel-titanium alloy. According to this embodiment, the size and/or shape of distal portion 136 may be predetermined by heat setting distal portion 136 to the desired diameter and length. Multiple embodiments of the invention incorporate alternate sizes and shapes of expansion member 132. For example, expansion member 132 may be heat set to expand so filter 111 has a larger diameter for one intervention and a smaller diameter for another.

Expansion member 132 may be completely or partially comprised of a radiopaque material. A radiopaque material is understood to be capable of producing a relatively bright image on a fluoroscopy screen or another imaging technique during a medical procedure. This relatively bright image aids the user of filter 111 in determining its location. Radiopaque materials may include gold, platinum, palladium, tantalum, tungsten alloy, and plastic material loaded with a radiopaque filler. Filter 111 and/or shaft 12 may further comprise additional radiopaque markers, similar to those known in the art.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method of filtering embolic debris from a blood vessel, comprising the steps of:

providing a elongate shaft having a filter frame coupled thereto, the filter frame having a filter material permeable to blood coupled thereto, the shaft having an expansion member disposed therein;

advancing the shaft to an area proximate a lesion within a blood vessel of a patient, the blood vessel having a lumen therethrough;

actuating the expansion member so as to shift the filter frame from a generally collapsed configuration to a generally expanded configuration such that the filter material conforms to the blood vessel lumen, wherein expanded the filter frame is generally cylindrical in shape and has a diameter and a length, the diameter being larger than the length;

performing an intravascular procedure that generates embolic debris;

capturing embolic debris with the filter material; and aspirating the filter material.

2. The method in accordance with claim 1, wherein the shaft comprises a catheter having a lumen extending therethrough and wherein the step of aspirating the filter material includes aspirating embolic debris through the lumen.

3. The method in accordance with claim 1, wherein the expansion member includes a proximal portion and a distal portion, and wherein the step of actuating the expansion member includes applying force in the distal direction to the proximal portion.

4. A method of filtering embolic debris from a renal artery, comprising the steps of:

providing a elongate shaft having a filter frame coupled thereto, the filter frame having a filter material permeable to blood coupled thereto, the shaft having an expansion member disposed therein;

advancing the shaft to the junction of a portion of the renal artery and a kidney, the renal artery having a lumen;

actuating the expansion member so as to shift the filter frame from a generally collapsed configuration to a generally expanded configuration such that the filter material conforms the renal artery lumen, wherein expanded the filter frame is generally cylindrical in shape and has a diameter and a length, the diameter being larger than the length;

performing an intravascular procedure that generates embolic debris;

capturing embolic debris with the filter material; and aspirating the filter material.

* * * * *

UNITED STATES PATENT AND TRADEMARK OFFICE
CERTIFICATE OF CORRECTION

PATENT NO. : 6,932,830 B2
APPLICATION NO. : 10/044354
DATED : August 23, 2005
INVENTOR(S) : Mark T. Ungs It is certified that error appears in the above-identified patent and that said Letters Patent is hereby corrected as shown below:

Column 4
Line 52, delete "conforms the", and insert therefor --conforms to the--.

Signed and Sealed this

Twenty-fourth Day of April, 2007

JON W. DUDAS
*Director of the United States Patent and Trademark Office*